(12) United States Patent
La et al.

(10) Patent No.: US 11,770,515 B2
(45) Date of Patent: *Sep. 26, 2023

(54) EXOSCOPE WITH ENHANCED DEPTH OF FIELD IMAGING

(71) Applicant: SYNAPTIVE MEDICAL INC., Toronto (CA)

(72) Inventors: William La, Toronto (CA); Siu Wai Jacky Mak, Toronto (CA)

(73) Assignee: Synaptive Medical Inc.

( * ) Notice: Subject to any disclaimer, the term of this patent is extended or adjusted under 35 U.S.C. 154(b) by 65 days.

This patent is subject to a terminal disclaimer.

(21) Appl. No.: 17/691,651

(22) Filed: Mar. 10, 2022

(65) Prior Publication Data

US 2022/0201268 A1 Jun. 23, 2022

Related U.S. Application Data

(63) Continuation of application No. 16/703,179, filed on Dec. 4, 2019, now Pat. No. 11,310,477, which is a (Continued)

(51) Int. Cl.
*H04N 13/239* (2018.01)
*G02B 27/10* (2006.01)
(Continued)

(52) U.S. Cl.
CPC ......... *H04N 13/239* (2018.05); *A61B 90/361* (2016.02); *A61B 90/37* (2016.02);
(Continued)

(58) Field of Classification Search
CPC .. H04N 13/239; H04N 13/156; H04N 13/296; H04N 2213/001; A61B 90/361;
(Continued)

(56) References Cited

U.S. PATENT DOCUMENTS

2012/0289816 A1* 11/2012 Mark ................... A61B 1/0615
    600/407
2014/0155757 A1* 6/2014 Yang .................. A61B 1/00188
    600/476
(Continued)

OTHER PUBLICATIONS

La, William, "Exoscope With Enhanced Depth of Field Imaging", U.S. Appl. No. 16/053,298, filed Aug. 2, 2018.
(Continued)

*Primary Examiner* — Oschta I Montoya

(57) ABSTRACT

An exoscope with enhanced depth of field imaging is provided. The exoscope includes first and second sets of optical devices, the first set having a fixed image plane, the second set having a variable image plane adjacent the fixed image plane of the first set. The second set includes at least one variable device configured to change the position of the variable image plane. A beamsplitter splits light from a combined optical path of the first and second set to respective image devices of the first and second set of optical devices. A controller controls the at least one variable device to change the position of the variable image plane relative to the fixed image plane, combines images acquired by the respective image devices, and controls a display device to render a combined image.

19 Claims, 14 Drawing Sheets

Related U.S. Application Data continuation of application No. 16/053,298, filed on Aug. 2, 2018, now Pat. No. 10,536,686.

(51) Int. Cl.
| | |
|---|---|
| *G02B 3/14* | (2006.01) |
| *G02B 27/14* | (2006.01) |
| *G02B 27/00* | (2006.01) |
| *H04N 13/156* | (2018.01) |
| *A61B 90/00* | (2016.01) |
| *H04N 13/296* | (2018.01) |

(52) U.S. Cl.
CPC ........... *G02B 3/14* (2013.01); *G02B 27/0075* (2013.01); *G02B 27/1013* (2013.01); *G02B 27/141* (2013.01); *H04N 13/156* (2018.05); *H04N 13/296* (2018.05); *A61B 2090/367* (2016.02); *A61B 2090/371* (2016.02); *A61B 2090/373* (2016.02)

(58) Field of Classification Search
CPC .............. A61B 90/37; A61B 2090/367; A61B 2090/371; A61B 2090/373; A61B 17/34; A61B 90/20; A61B 90/50; A61B 2034/2051; A61B 2034/2055; A61B 1/00163; A61B 1/045; G02B 3/14; G02B 27/0075; G02B 27/1013; G02B 27/141; G02B 21/22; G02B 21/0012; G02B 21/367

See application file for complete search history.

(56) References Cited

U.S. PATENT DOCUMENTS

| | | | |
|---|---|---|---|
| 2015/0085093 A1* | 3/2015 | Heni | A61B 1/00114 |
| | | | 348/65 |
| 2015/0185414 A1* | 7/2015 | Baumann | G02B 6/4204 |
| | | | 362/553 |
| 2017/0209050 A1* | 7/2017 | Fengler | A61B 1/043 |
| 2018/0077404 A1* | 3/2018 | Bechtel | G03B 35/10 |
| 2018/0125586 A1* | 5/2018 | Sela | A61B 5/00 |
| 2018/0270466 A1* | 9/2018 | Heni | H04N 13/296 |
| 2018/0368656 A1* | 12/2018 | Austin | A61B 1/0004 |
| 2019/0014979 A1* | 1/2019 | Czupalla | A61B 1/00183 |
| 2019/0021576 A1* | 1/2019 | Hale | A61B 1/0655 |

OTHER PUBLICATIONS

La, William, "Exoscope With Enhanced Depth of Field Imaging", U.S. Appl. No. 16/703,179, filed Dec. 4, 2019.

\* cited by examiner

EXOSCOPE WITH ENHANCED DEPTH OF FIELD IMAGING

CROSS-REFERENCE TO RELATED APPLICATIONS

This application is a continuation of U.S. patent application Ser. No. 16/703,179, filed Dec. 4, 2019, which is a continuation of U.S. patent application Ser. No. 16/053,298 filed Aug. 2, 2018, contents of both incorporated herein by reference.

FIELD

The specification relates generally to exoscopes and specifically an exoscope with enhanced depth of field imaging.

BACKGROUND

A surgical microscope is an essential tool in many surgical procedures including those in spine and brain. With advances in optics and the digital microscope, surgeons are now operating with more visualization power, including higher resolution and higher magnification, allowing surgeons to see finer details in the surgical field. However, there is one fundamental trade-off in any surgical microscope: the higher the magnification and optical resolution that the surgeon utilizes, the smaller the depth of field (i.e. smaller the field of focus in the depth direction). This is problematic as surgeons require anatomical landmarks in the vicinity of the surgical site to be in focus to provide depth cues and context while operating.

SUMMARY

The present disclosure is generally directed to an exoscope with enhanced depth of field imaging. The exoscope provided herein includes two optical paths that image the same region of a sample, for example tissue. A first optical path has a fixed optical path length and hence a fixed image plane and fixed depth of field, while the second optical path has a variable optical path length and hence a variable image plane and a variable depth of field. The two optical paths partially overlap using a beamsplitter. The variable optical path length may be achieved using a varifocal lens, such as a liquid-based varifocal lens and/or a moveable plenoptic array of lenses and/or an optic wheel and/or a moveable lens and/or a moveable sensor. Images from the two optical paths are combined and rendered at a display screen.

Hence, the techniques described herein are generally compatible with image guided medical procedures using an access port. This port-based surgery approach allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue. The techniques described herein may assist a surgeon performing brain surgery, and the like, via an access port in determining locations of organized tissue in a brain.

Provided herein is an exoscope comprising: a first set of optical devices, forming a first optical path having a fixed path length and a fixed image plane, including a first image detector configured to acquire a first image at the fixed image plane; a second set of optical devices, forming a second optical path having a variable optical path length and a variable image plane adjacent the fixed image plane of the first set of optical devices, the second set of optical devices including: a second image detector configured to acquire a second image at the variable image plane; and at least one variable device configured to change a length of the variable optical path length and position of the variable image plane relative to the fixed image plane; a beamsplitter positioned in both the first optical path and the second optical path, the beamsplitter configured to: combine the first optical path and the second optical path between the beamsplitter and both the fixed image plane and the variable image plane; and direct respective light from each of the first optical path and the second optical path respectively towards the first image detector and the second image detector; a display device; and a controller configured to: control the at least one variable device to change the length of the variable optical path length and the position of the variable image plane relative to the fixed image plane; control the first image detector to acquire the first image at the fixed image plane; control the second image detector to acquire the second image at the variable image plane; generate a combined image of the first image and the second image; and control the display device to render the combined image.

BRIEF DESCRIPTIONS OF THE DRAWINGS

For a better understanding of the various implementations described herein and to show more clearly how they may be carried into effect, reference will now be made, by way of example only, to the accompanying drawings in which.

DETAILED DESCRIPTION

Figure 1:
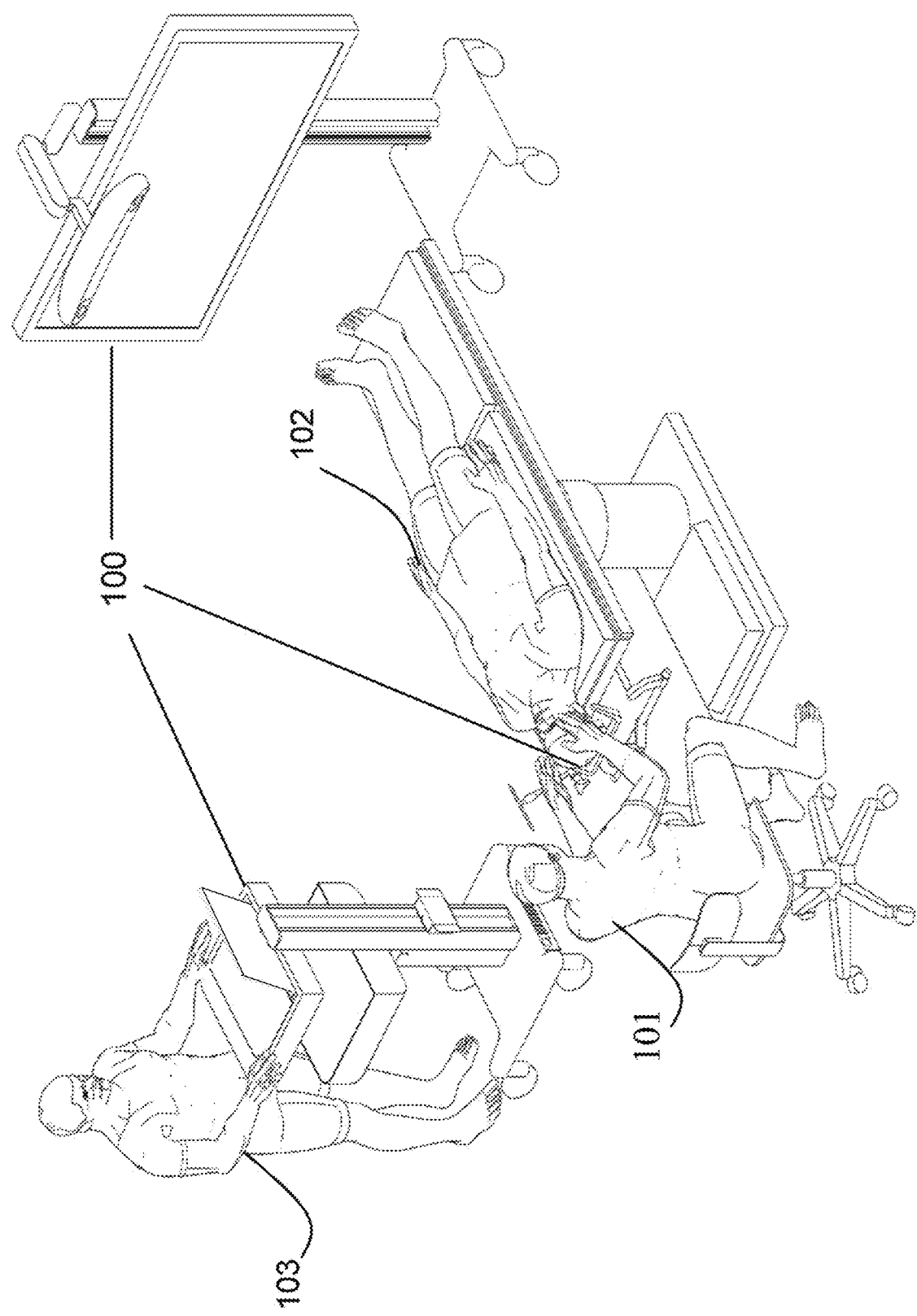
FIG. 1 shows an example operating room setup for a minimally invasive access port-based medical procedure, according to non-limiting implementations.

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

The systems and methods described herein may be useful in the field of neurosurgery, including oncological care, neurodegenerative disease, stroke, brain trauma and orthopedic surgery; however, persons of skill will appreciate the ability to extend these concepts to other conditions or fields of medicine. It should be noted that the surgical process is applicable to surgical procedures for brain, spine, knee and any other suitable region of the body.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, XZ, and the like). Similar logic may be applied for two or more items in any occurrence of "at least one . . . " and "one or more . . . " language.

The terms "about", "substantially", "essentially", "approximately", and the like, are defined as being "close to", for example as understood by persons of skill in the art. In some implementations, the terms are understood to be "within 10%," in other implementations, "within 5%", in yet further implementations, "within 1%", and in yet further implementations "within 0.5%".

Referring to FIG. 1, a non-limiting example navigation system 100 is shown to support minimally invasive access port-based surgery. In FIG. 1, a neurosurgeon 101 conducts a minimally invasive port-based surgery on a patient 102 in an operating room (OR) environment. The navigation system 100 includes an equipment tower, tracking system, displays and tracked instruments to assist the surgeon 101 during the procedure. An operator 103 may also be present to operate, control and provide assistance for the navigation system 100.

Figure 2:
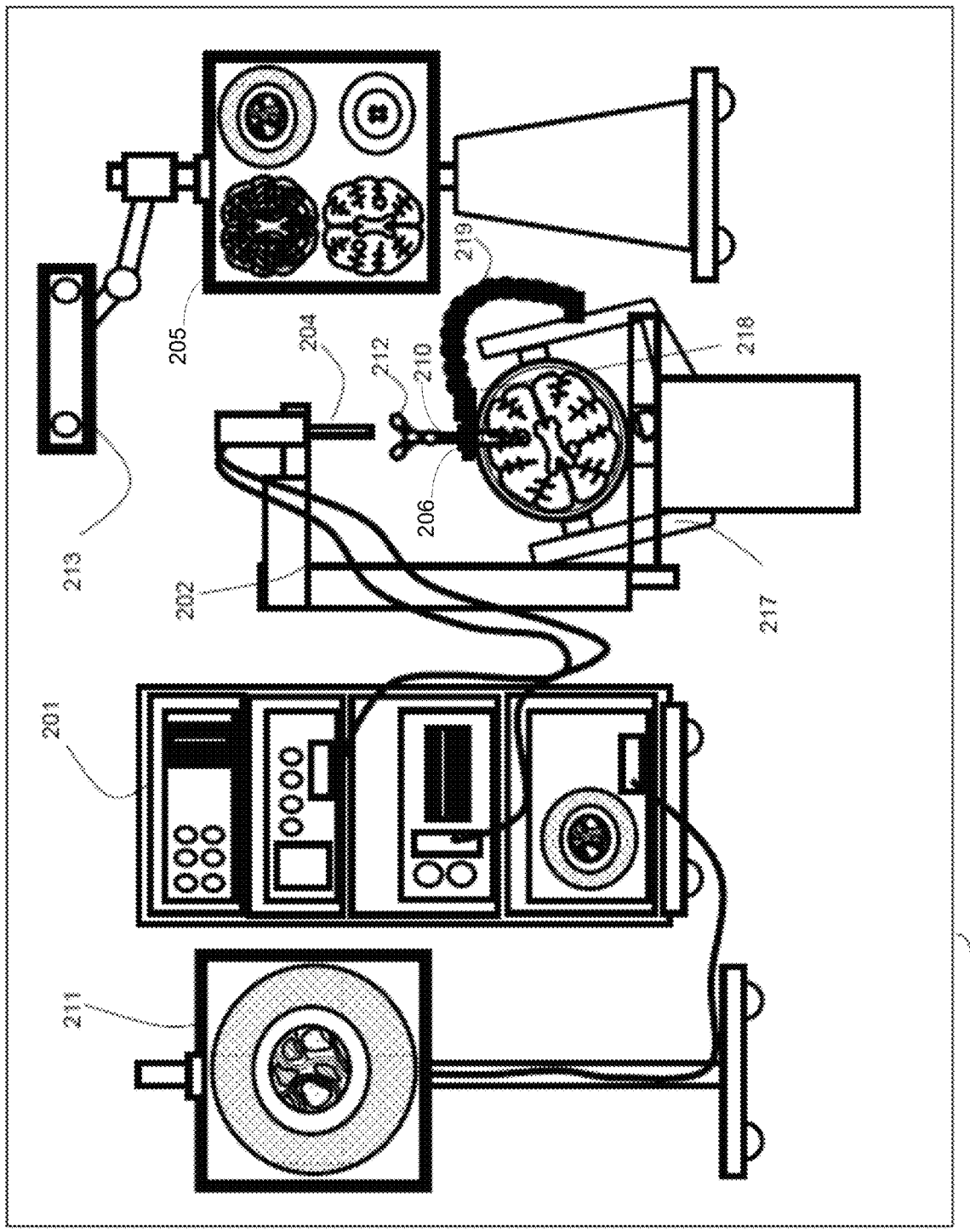
FIG. 2 is an example illustration of a medical navigation system that may be used to implement a surgical plan for a minimally invasive surgical procedure, according to non-limiting implementations.

Referring to FIG. 2, a diagram is shown illustrating components of an example medical navigation system 200, according to non-limiting implementations. The medical navigation system 200 illustrates a context in which a surgical plan including equipment (e.g., tool and material) tracking, such as that described herein, may be implemented. The medical navigation system 200 includes, but is not limited to, one or more monitors 205, 211 for displaying a video image, an equipment tower 201, and a mechanical arm 202, which supports an optical scope 204. The equipment tower 201 may be mounted on a frame (e.g., a rack or cart) and may contain a computer or controller (examples provided with reference to FIGS. 3 and 6 below), planning software, navigation software, a power supply and software to manage the mechanical arm 202, and tracked instruments. In one example non-limiting implementation, the equipment tower 201 may comprise a single tower configuration with dual display monitors 211, however other configurations may also exist (e.g., dual tower, single display, etc.). Furthermore, the equipment tower 201 may also be configured with a universal power supply (UPS) to provide for emergency power, in addition to a regular AC adapter power supply.

A patient's anatomy may be held in place by a holder. For example, in a neurosurgical procedure the patient's head may be held in place by a head holder 217, and an access port 206 and an introducer 210 may be inserted into the patient's head. The introducer 210 may be tracked using a tracking camera 213, which provides position information for the navigation system 200. The tracking camera 213 may also be used to track tools and/or materials used in the surgery, as described in more detail below. In one example non-limiting implementation, the tracking camera 213 may comprise a 3D (three-dimensional) optical tracking stereo camera, similar to one made by Northern Digital Imaging (NDI), configured to locate reflective sphere tracking markers 212 in 3D space. In another example, the tracking camera 213 may comprise a magnetic camera, such as a field transmitter, where receiver coils are used to locate objects in 3D space, as is also known in the art. Location data of the mechanical arm 202 and access port 206 may be determined by the tracking camera 213 by detection of tracking markers 212 placed on these tools, for example the introducer 210 and associated pointing tools. Tracking markers may also be placed on surgical tools or materials to be tracked. The secondary display 205 may provide output of the tracking camera 213. In one example non-limiting implementation, the output may be shown in axial, sagittal and coronal views as part of a multi-view display.

As noted above with reference to FIG. 2, the introducer 210 may include tracking markers 212 for tracking. The tracking markers 212 may comprise reflective spheres in the case of an optical tracking system and/or pick-up coils in the case of an electromagnetic tracking system. The tracking markers 212 may be detected by the tracking camera 213 and their respective positions are inferred by the tracking software.

As shown in FIG. 2, a guide clamp 218 (or more generally a guide) for holding the access port 206 may be provided. The guide clamp 218 may optionally engage and disengage with the access port 206 without needing to remove the access port 206 from the patient. In some examples, the access port 206 may be moveable relative to the guide clamp 218, while in the guide clamp 218. For example, the access port 206 may be able to slide up and down (e.g., along the longitudinal axis of the access port 206) relative to the guide clamp 218 while the guide clamp 218 is in a closed position. A locking mechanism may be attached to or integrated with the guide clamp 218, and may optionally be actuatable with one hand, as described further below. Furthermore, an articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

Figure 3:
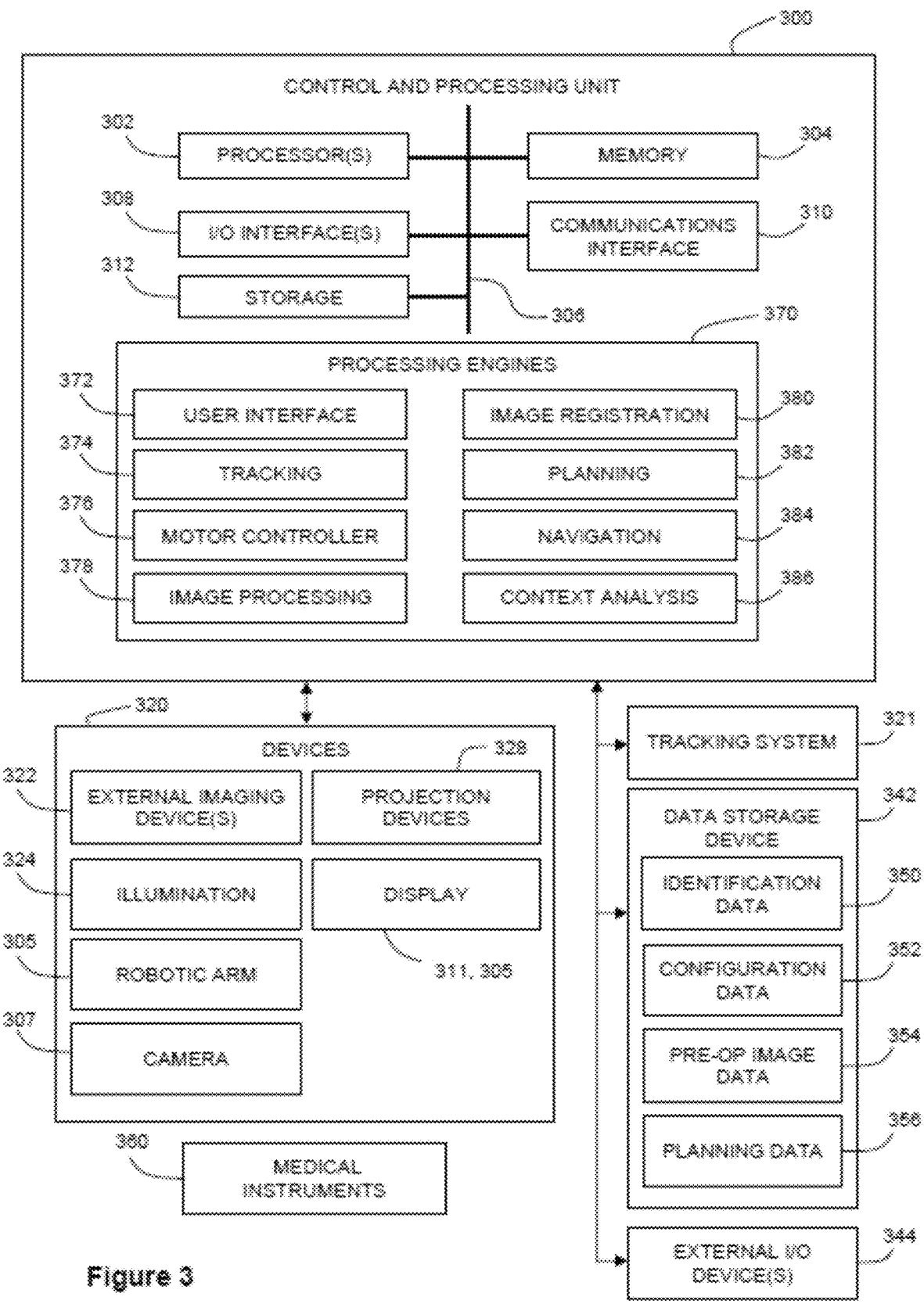
FIG. 3 depicts a block diagram illustrating components of a planning system used to plan a medical procedure that may then be implemented using the navigation system of FIG. 2, according to non-limiting implementations.

Referring to FIG. 3, a block diagram is shown illustrating a control and processing unit 300 that may be used in the navigation system 200 of FIG. 2 (e.g., as part of the equipment tower). In one example non-limiting implementation, control and processing unit 300 may include one or more processors 302, a memory 304, a system bus 306, one or more input/output interfaces 308, a communications interface 310, and storage device 312. In particular, one or more processors 302 may comprise one or more hardware processors and/or one or more microprocessors. Control and processing unit 300 may be interfaced with other external devices, such as tracking system 321, data storage device 342, and external user input and output devices 344, which may include, but is not limited to, one or more of a display, keyboard, mouse, foot pedal, and microphone and speaker. Data storage device 342 may comprise any suitable data storage device, including, but not limited to a local and/or remote computing device (e.g. a computer, hard drive, digital media device, and/or server) having a database stored thereon. In the example shown in FIG. 3, data storage device 342 includes, but is not limited to, identification data 350 for identifying one or more medical instruments 360 and configuration data 352 that associates customized configuration parameters with one or more medical instruments 360. Data storage device 342 may also include, but is not limited to, preoperative image data 354 and/or medical procedure planning data 356. Although data storage device 342 is shown as a single device in FIG. 3, in other implementations, data storage device 342 may be provided as multiple storage devices.

Medical instruments 360 may be identifiable using control and processing unit 300. Medical instruments 360 may be connected to and controlled by control and processing unit 300, and/or medical instruments 360 may be operated and/or otherwise employed independent of control and processing unit 300. Tracking system 321 may be employed to track one or more of medical instruments 360 and spatially register the one or more tracked medical instruments 360 to an intraoperative reference frame. In another example, a sheath may be placed over a medical instrument 360 and the sheath may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include, but are not limited, one or more external image devices 322, one or more illumination devices 324, a robotic arm 305, one or more projection devices 328, and one or more displays 305, 311.

Aspects of the specification may be implemented via processor(s) 302 and/or memory 304. For example, the functionalities described herein may be partially implemented via hardware logic in processor 302 and partially using the instructions stored in memory 304, as one or more processing modules 370 and/or processing engines. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example non-limiting implementation the processing modules 370 may be stored in the memory 304 and the processing modules may be collectively referred to as processing modules 370.

It is to be understood that the system is not intended to be limited to the components shown in FIG. 3. One or more components of the control and processing unit 300 may be provided as an external component or device. In one example non-limiting implementation, navigation engine 384 may be provided as an external navigation system that is integrated with control and processing unit 300.

Some implementations may be implemented using processor 302 without additional instructions stored in memory 304. Some implementations may be implemented using the instructions stored in memory 304 for execution by one or more general purpose microprocessors. Thus, the specification is not limited to a specific configuration of hardware and/or software.

While some implementations may be implemented in fully functioning computers and computer systems, various implementations are capable of being distributed as a computing product in a variety of forms and are capable of being applied regardless of the particular type of machine or computer readable media used to actually effect the distribution.

At least some aspects disclosed may be embodied, at least in part, in software. That is, the techniques may be carried out in a computer system or other data processing system in response to its processor, such as a microprocessor, executing sequences of instructions contained in a memory, such as read only memory (ROM), volatile random access memory (RAM), non-volatile memory, cache and/or a remote storage device.

A computer readable storage medium, and/or a non-transitory computer readable storage medium, may be used to store software and data which, when executed by a data processing system, causes the system to perform various methods. The executable software and data may be stored in various places including for example ROM, volatile RAM, non-volatile memory and/or cache. Portions of this software and/or data may be stored in any one of these storage devices.

Examples of computer-readable storage media include, but are not limited to, recordable and non-recordable type media such as volatile and non-volatile memory devices, ROM, RAM, flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical and/or other forms of propagated signals, such as carrier waves, infrared signals, digital signals, and the like. The storage medium may comprise the internet cloud, storage media therein, and/or a computer readable storage medium and/or a non-transitory computer readable storage medium, including, but not limited to, a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB (Universal Serial Bus) keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 200, which may include control and processing unit 300, is to provide tools to a surgeon and/or a neurosurgeon that will lead to the most informed, least damaging neurosurgical operations. In addition to removal of brain tumours and intracranial hemorrhages (ICH), the navigation system 200 may also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present specification may be applied to other suitable medical procedures.

Figure 4:
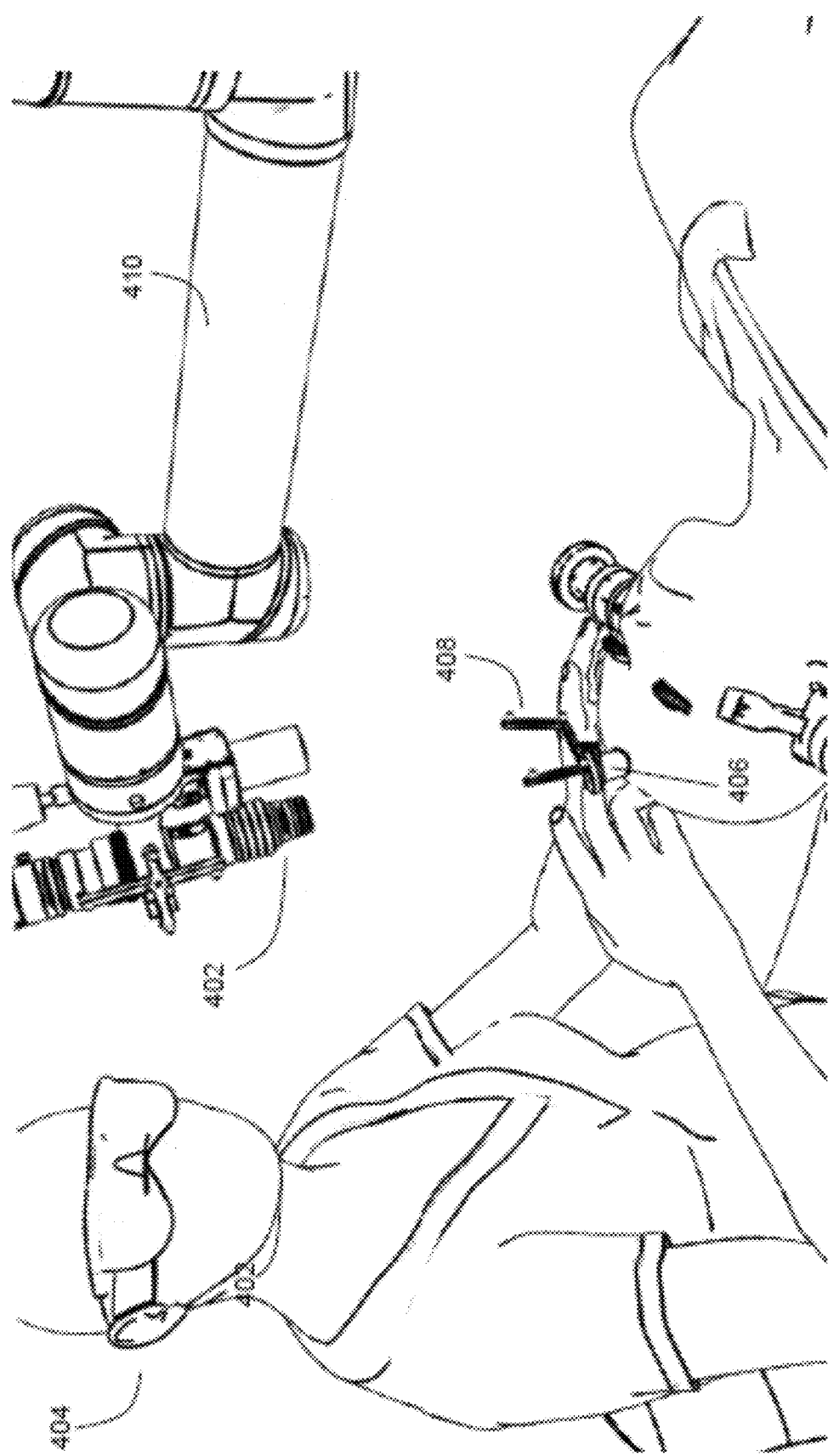
FIG. 4 depicts an example implementation port based brain surgery using a video scope, according to non-limiting implementations.

Attention is next directed to FIG. 4 which depicts a non-limiting example of a port-based brain surgery procedure using a video scope. In FIG. 4, operator 404, for example a surgeon, may align video scope 402 to peer down port 406. Video scope 402 may be attached to an adjustable mechanical arm 410. Port 406 may have a tracking tool 408 attached to it where tracking tool 408 is tracked by a tracking camera of a navigation system.

Even though the video scope 402 may comprise an exoscope and/or a microscope, these devices introduce optical and ergonomic limitations when the surgical procedure is conducted over a confined space and conducted over a prolonged period such as the case with minimally invasive brain surgery.

Figure 5:
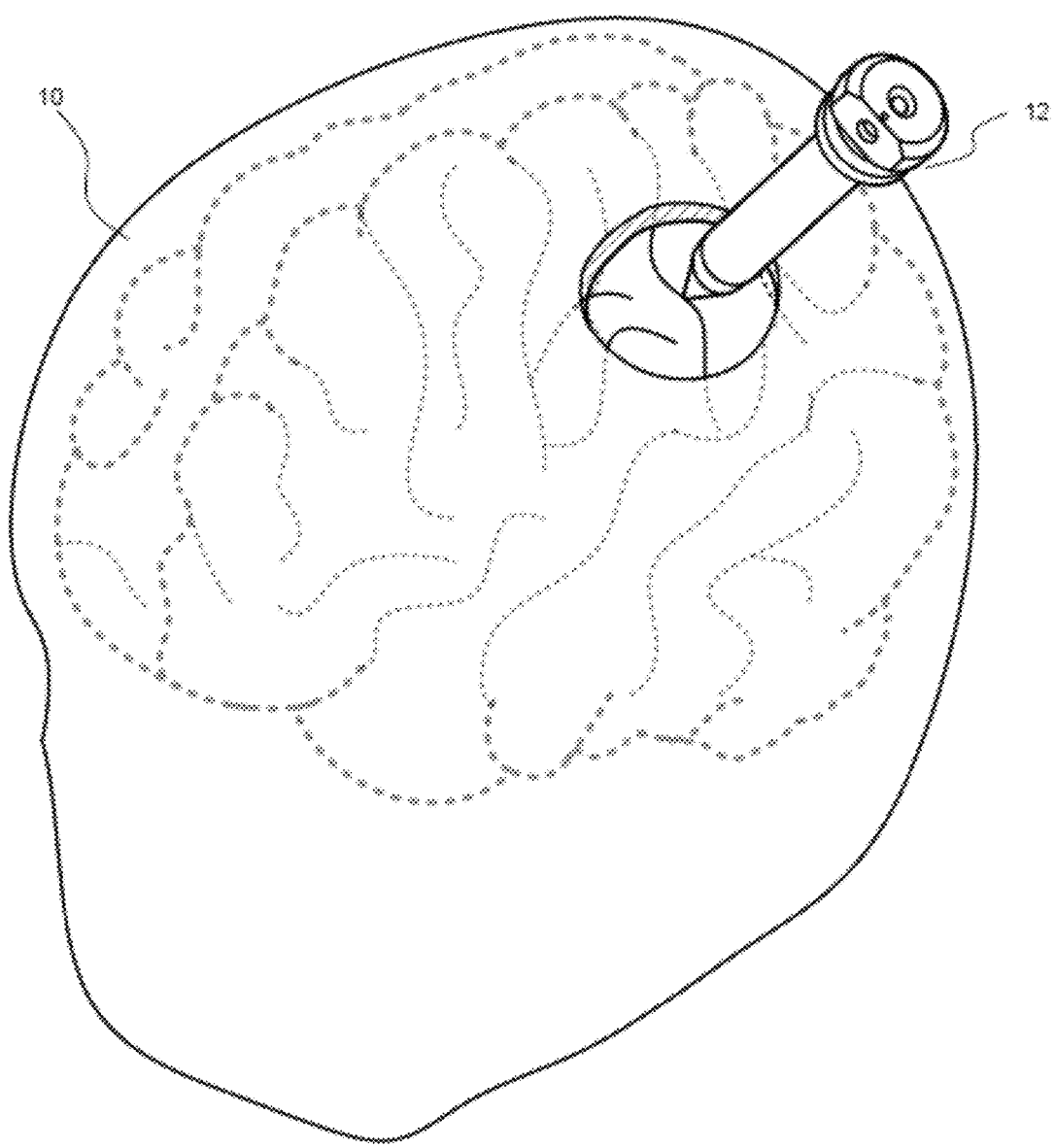
FIG. 5 depicts insertion of an access port into a human brain, for providing access to interior brain tissue during a medical procedure, according to non-limiting implementations.

FIG. 5 illustrates the insertion of an access port 12 into a human brain 10, in order to provide access to interior brain tissue during a medical procedure. In FIG. 5, access port 12 is inserted into a human brain 10, providing access to interior brain tissue. Access port 12 may include, but is not limited to, instruments such as catheters, surgical probes, and/or cylindrical ports such as the NICO BrainPath®.

Surgical tools and instruments may then be inserted within a lumen of the access port 12 in order to perform surgical, diagnostic or therapeutic procedures, such as resecting tumors as necessary. However, the present specification applies equally well to catheters, DB S needles, a biopsy procedure, and also to biopsies and/or catheters in other medical procedures performed on other parts of the body.

In the example of a port-based surgery, a straight and/or linear access port 12 is typically guided down a sulci path of the brain. Surgical instruments and/or surgical tools would then be inserted down the access port 12.

Figure 6:
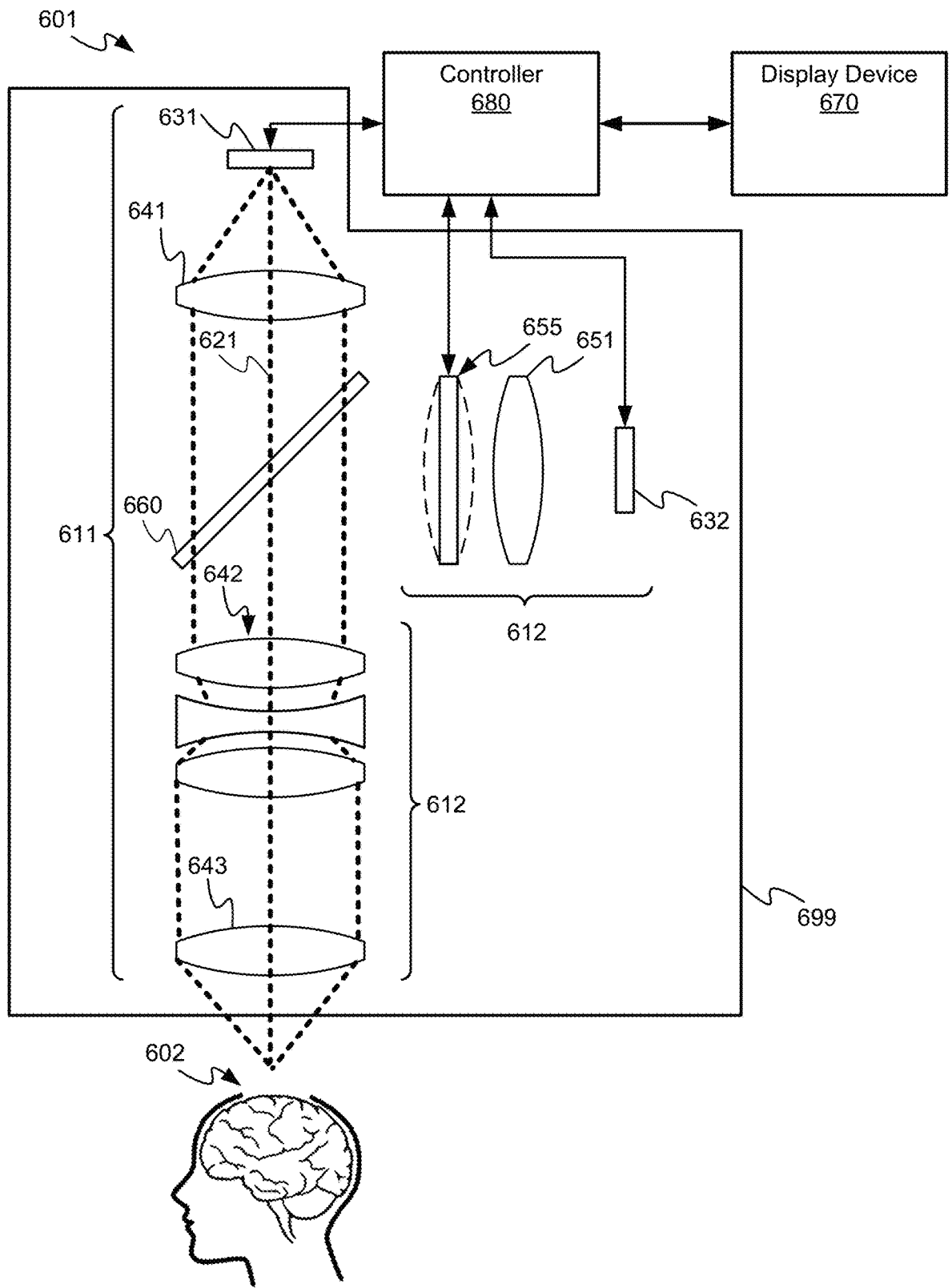
FIG. 6 depicts a side schematic view of an exoscope with enhanced depth of field imaging, and an optical path of a first set of optical devices, according to non-limiting implementations.
Figure 7:
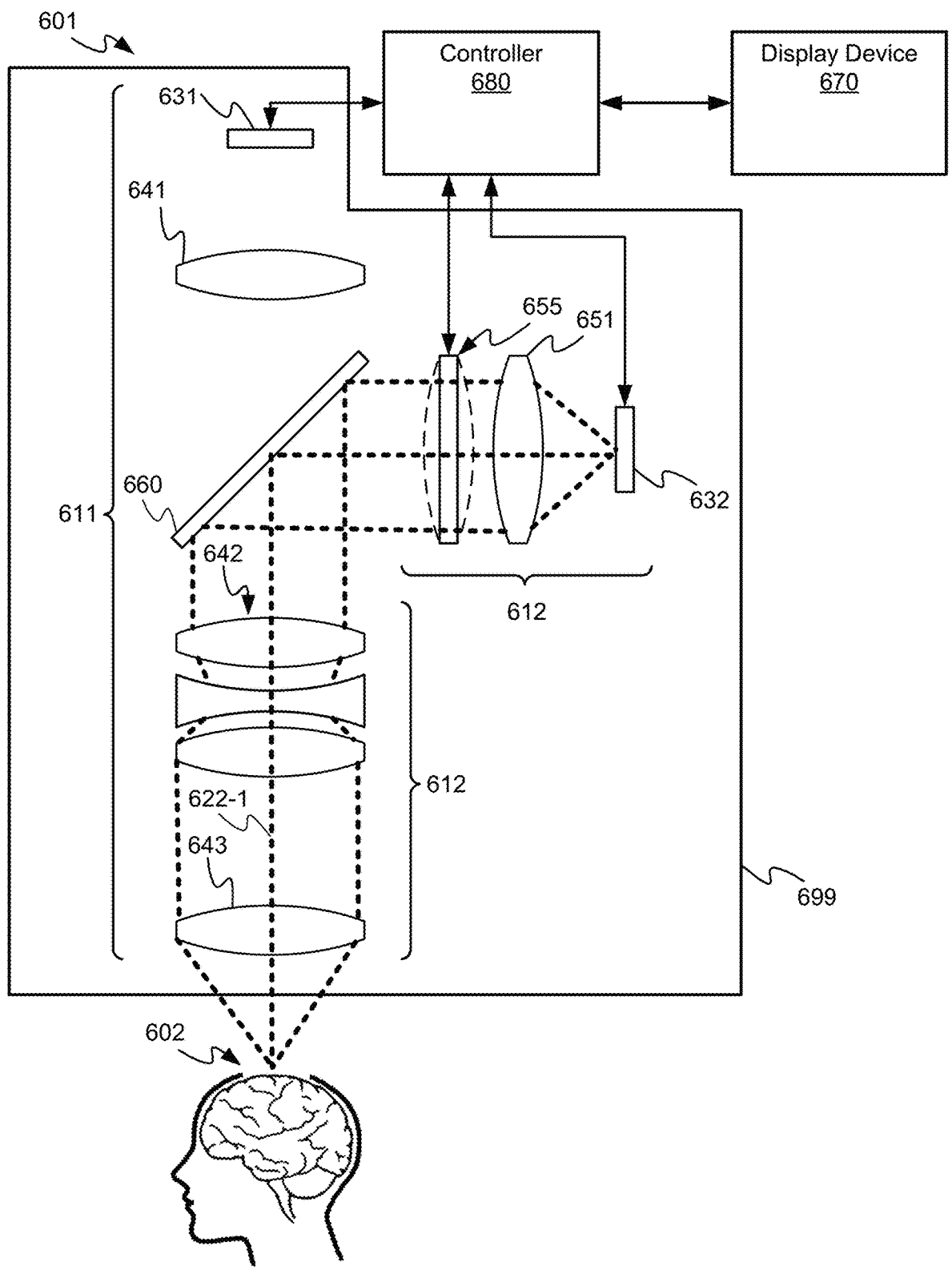
FIG. 7 depicts the exoscope of FIG. 6, and an optical path of a second set of optical devices in a parallel plane mode, according to non-limiting implementations.
Figure 8:
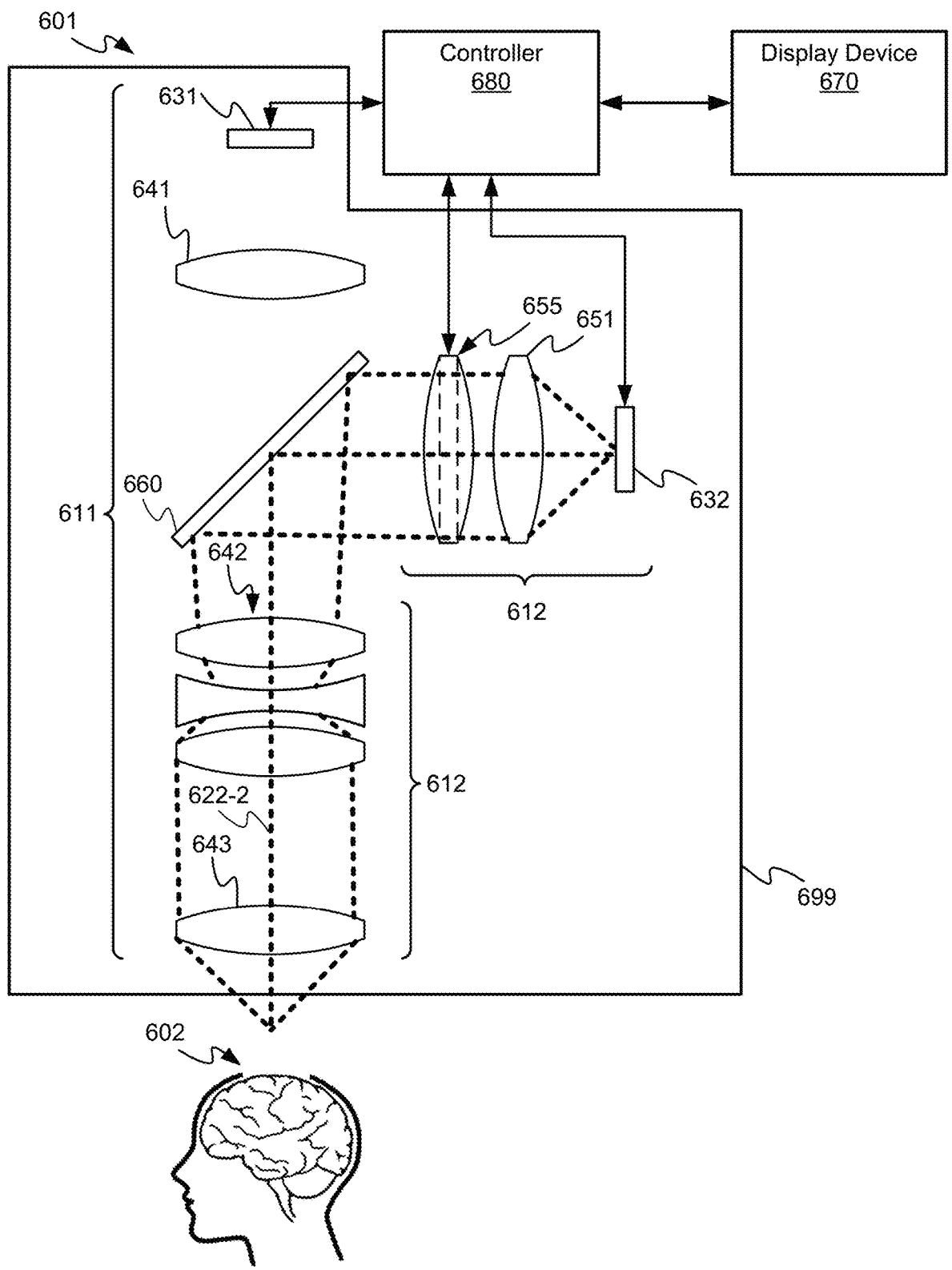
FIG. 8 depicts the exoscope of FIG. 6, and an optical path of the second set of optical devices in a lens mode, according to non-limiting implementations.

Attention is next directed to FIG. 6, FIG. 7, and FIG. 8 each of which depict a side schematic view of an example exoscope 601 with enhanced depth of field imaging, that could be used with the access port 12 and/or in open case surgery, for example to image a sample 602, as depicted a human brain (such as the human brain 10).

The exoscope 601 comprises a first set of optical devices 611 and a second set of optical devices 612. The first set of optical devices 611 form a first optical path 621 having a fixed optical path length and a fixed image plane, and the second set of optical devices 612 form a second optical path 622 having a variable optical path length and a variable image plane (e.g. see FIG. 9, described below).

While in FIG. 6, FIG. 7, and FIG. 8, the optical paths 621, 622 are not focused directly at a surface of the sample 602, it is understood that this depiction is for clarity only and the optical paths 621, 622 are generally focused at the surface of the sample 602.

As explained in detail below, the second set of optical devices 612 includes at least one variable device configured to change a length of the variable optical path length of the second set of optical devices 612 and a position of the variable image plane relative to the fixed image plane of the first set of optical devices 611.

For clarity, FIG. 6 depicts the first optical path 621 of the first set of optical devices 611, FIG. 7 depicts a second optical path 622-1 of the second set of optical devices 612 in a first configuration of the variable device of the second set of optical devices 612, and FIG. 8 depicts a further second optical path 622-2 of the second set of optical devices 612 in a second configuration of the variable device of the second set of optical devices 612. The two second optical paths 622-1, 622-2 will be interchangeably referred to, collectively as the second optical paths 622 and, generically, as the second optical path 622.

Furthermore, as depicted, a center dashed line of each of the optical paths 621, 622 show a general path through each of the sets of optical devices 611, 612, while the two dashed outer lines of each of the optical paths (e.g. on either side of the center dashed line) generally show focusing and the like by lenses, and the like, of each of the sets of optical devices 611, 612. Hence, together, the three lines of each of the optical paths 621, 622, show the general behavior of light and/or images via the optical paths 621, 622.

The components of the exoscope 601 will next be described with reference to any of FIG. 6, FIG. 7 and FIG. 8, though a description of the first optical path 621 is with reference to FIG. 6 and a description of the optical paths 622 is with reference to FIG. 7 and FIG. 8.

The first set of optical devices 611 comprises a first image detector 631 configured to acquire a first image at the fixed image plane (e.g. see FIG. 9, described below) of the first set of optical devices 611. Similarly, the second set of optical devices 612 comprises a second image detector 632 configured to acquire a second image at the variable image plane of the second set of optical devices 612. Each of the image detectors 631, 632 may comprise a charge-coupled device (CCD) and the like, though any type of suitable image detector is within the scope of the present specification including, but not limited to, image detectors that are detect specific wavelengths and/or wavelength ranges; for example, one or both of the image detectors 631, 632 may be configured to detect fluorescence in the sample 602. In these examples, one image detector 631, 632 may be configured to detect fluorescence, and the other image detector 632, 631 may be configured to detect images in wavelength ranges visible to a human vision system (e.g. such as white light images and/or color images) in which an overlay between a white light image and a fluorescence image could be formed. In some of these examples, the image detector 631 configured to acquire images at the fixed image plane may be used to acquire white light images, while the image detector 632 configured to acquire images at the variable image plane may be used to acquire fluorescence images (e.g. since a fluorescence image may not provide as many resolution details a as white light image, and the images at the variable image plane may be slightly out of focus and/or more regions in the images at the variable image plane may be slightly out of focus as compared to the images at the fixed image plane). Hence, a person of skill in the art understands that the first image detector 631 and the second image detector 632 may have different respective wavelength sensitivity ranges.

The first set of optical devices 611 are generally configured to image the sample 602 onto the image detector 631. As depicted, the first set of optical devices 611 further comprises a focusing lens 641, one or more zoom lenses 642 and an objective lens 643. However, other configurations of optical devices are within the scope of the present specification and the first set of optical devices 611 may include other lenses and/or different lenses, mirrors, prisms and/or any type of optical device for imaging the sample 602 onto the image detector 631.

In general images acquired by the first image detector 631 are focused onto the first image detector 631 by the focusing lens 641, the zoom lens 642 provides a fixed optical zoom for the exoscope 601, and the objective lens 643 acquires images in an image plane at least partially defined by the focal length of the objective lens 643.

Similarly, the second set of optical devices 612 are generally configured to image the sample 602 onto the image detector 632. As depicted, the second set of optical devices 612 further comprises a focusing lens 651 and the one or more zoom lenses 642 and the objective lens 643.

In general images acquired by the second image detector 632 are focused onto the second image detector 632 by the focusing lens 651.

Other configurations of optical devices are within the scope of the present specification and the second set of optical devices 612 may include other lenses and/or different lenses, mirrors, prisms and/or any type of optical device for imaging the sample 602 onto the image detector 632.

However, the second set of optical devices 612 further comprises, at least one variable device 655 configured to change a length of the variable optical path length (e.g. of the second optical path 622) and a position of the variable image plane relative to the fixed image plane of the first set of optical devices 611. The variable device 655 may comprise one or more of a varifocal lens having a variable focal length, a liquid-based varifocal lens configured to change between a parallel plane mode and a lens mode, a moveable lens and an apparatus for moving the moveable lens along the second optical path 622, an apparatus for moving the second image detector 632 along the second optical path, and the like.

However, with reference to FIG. 7 and FIG. 8, as depicted, the at least one variable device 655 comprises a varifocal lens having a variable focal length for example by changing a thickness and/or curvature of the varifocal lens. Hence, by changing the focal length of the varifocal lens, the focal length changes and hence the optical length of the second optical path 622 changes.

In some examples, the varifocal lens may include a bendable and/or malleable and/or deformable portion which, when deformed (e.g. via a voicecoil, and the like), and the like, changes the focal length.

However, as specifically depicted in FIG. 7 and FIG. 8, the at least one variable device 655 may comprise a liquid-based varifocal lens configured to change between a parallel plane mode and a lens mode.

For example, in FIG. 7 (and FIG. 6), the at least one variable device 655 is depicted as a liquid-based varifocal lens in a parallel plane mode, as the shape of the liquid-based varifocal lens is a parallel plane with a center of the second optical path 622 being normal to the faces of the liquid-based varifocal lens.

However, in FIG. 8, the at least one variable device 655 is depicted as a liquid-based varifocal lens in a lens mode; for example, in FIG. 8, an electrical current may have been applied to a voice coil contained in a liquid-based varifocal lens to change the shape from a parallel plane (as in FIG. 7) to a lens.

To contrast the changing shape of the liquid-based varifocal lens (e.g. the at least one variable device 655), in FIG. 7, the shape of the liquid-based varifocal lens in the parallel plane mode is depicted in solid lines and the shape of the liquid-based varifocal lens in the lens mode is depicted in dashed lines; similarly, in FIG. 8, the shape of the liquid-based varifocal lens in the lens mode is depicted in solid lines and the shape of the liquid-based varifocal lens in the parallel plane mode is depicted in dashed lines.

It is understood by persons of skill in the art that the focal length of the least one variable device 655 depicted in FIG. 7 is infinite (e.g. such that the focusing lens 651, the zoom lens 642 and the objective lens 643 define the optical path length of the second optical path 622-1 in FIG. 7), whereas the focal length of the least one variable device 655 depicted in FIG. 8 is not infinite (e.g. such that focusing lens 651, the least one variable device 655, the zoom lens 642 and the objective lens 643 define the optical path length of the second optical path 622-2 in FIG. 8). Hence, by varying the focal length of the least one variable device 655, the length of the second optical path 622 of the second set of optical devices 612 may be varied, as well as a position of an image plane of the second optical path 622.

In some examples, the focal length of the least one variable device 655 may be smoothly varied and/or varied in an analog fashion, and hence a length of the optical path 622 of the second set of optical devices 612 may be smoothly varied to select a length of the length of the second optical path 622. For example, if the lens mode of the liquid-based varifocal lens in FIG. 8 shows a maximum amount of liquid that may be in the liquid-based varifocal lens, and if the parallel plane mode of the liquid-based varifocal lens in FIG. 7 shows a minimum amount of liquid that may be in the liquid-based varifocal lens, a length of the second optical path 622 of the second set of optical devices 612 may be smoothly varied between the two modes and two focal lengths etc., and by changing the amount of liquid in the liquid-based varifocal lens.

Control of the least one variable device 655 will be described in more detail below.

As will now be apparent, the first set of optical devices 611 and the second set of optical devices 612 share the zoom lens 642 and the objective lens 643 and an overlapping portion of the optical paths 621, 622 each include the shared lenses 642, 643. However, to ensure that respective light from each of the optical paths 621, 622 are directed to the respective image detectors 631, 632, the exoscope 601 further comprises a beamsplitter 660 positioned in both the first optical path 621 and the second optical path 622, the beamsplitter 660 configured to: combine the first optical path 621 and the second optical path 622 between the beamsplitter 660 and both the fixed image plane of the first set of optical devices 611 and the variable image plane of the second set of optical devices 622; and direct respective light from each of the first optical path 621 and the second optical path 622 respectively towards the first image detector 631 and the second image detector 632.

As depicted, the portion of the second optical path 622 that does not overlap with the first optical path 621 is at about 90° to the first optical path 621. Hence, the beamsplitter 660 is at 45° to each of the optical paths 621, 622.

For example, the beamsplitter 660 may comprise a 50/50 beam splitter and the like. However, when each of the image detectors 631, 632 are to image different wavelength ranges, the beamsplitter 660 may comprise an optical filter, such as a dichroic filter, and the like, configured to transmit wavelengths to be imaged by the first image detector 631 and reflect wavelengths to be imaged by the second image detector 632.

Hence, in general, the combination of the first set of optical devices 611, the second set of optical devices 612, the beamsplitter 660 and the image detectors 631, 632 produce at least two images of the sample 602: a first image produced by the first set of optical devices 611 and the first image detector 631, and a second image produced by the second set of optical devices 612 and the second image detector 632. As the at least one variable device 655 may be controlled to change a length of the optical path length of the second optical path 622, and hence also change a position of the image plane of the second optical path 622 relative to the fixed image plane of the first optical path 621, the second image generally has a different depth of focus than the first image. These images may be combined to produce an image with an extended depth of field that may be the combination of the depths of field of the two images.

For example, as depicted, the exoscope 601 further comprises: a display device 670 and a controller 680. The display device 670 may be one of more of the displays 305, 311; however, the display device 670 may be a component of a surgical computer, a heads-up display (HUD) device, and the like. The controller 680 may comprise one or more hardware processors, one or more microcontrollers, one or more microprocessor, and the like including, but not limited to, the one or more processors 302. As depicted, the controller 302 is in communication with the display device 670, the image detectors 631, 632 and the at least one variable device 655 via respective wired and/or wireless links depicted as arrows in the figures.

In general, the controller 680 is configured to: control the at least one variable device 655 to change the length of the variable optical path length of the second set of optical devices 612 and the position of the variable image plane of the second set of optical devices 612 relative to the fixed image plane of the first set of optical devices 611; control the first image detector 631 to acquire a first image at the fixed image plane; control the second image detector 632 to acquire a second image at the variable image plane; generate a combined image of the first image and the second image; and control the display device 670 to render the combined image.

For example, a surgeon operating on a patient may interact with an input device (such as a point device, a graphic user interface at the display device 670, and the like) in communication with the controller 680, to cause the controller 680 to control the at least one variable device 655 to change the length of the variable optical path length of the second set of optical devices 612 and the position of the variable image plane of the second set of optical devices 612 relative to the fixed image plane of the first set of optical devices 611. For example, the surgeon may interact with the input device to select an image plane of the second set of optical devices 612. While not depicted, it is understood by persons of skill in the art that the at least one variable device 655 comprises suitable devices to control the focal length, and the like (e.g. a deformable membrane controllable with an electrically controlled voice coil and the like) which communicate with the controller 680 to change the length of the variable optical path length of the second set of optical devices 612 and the position of the variable image plane of the second set of optical devices 612 relative to the fixed image plane of the first set of optical devices 611. Once the variable image plane is selected, the controller 680 acquires images from the image detectors 631, 632, combines the images and controls the display device 670 to render a combined image. In some examples, described below, the display device 670 may be alternatively controlled to render one or more of the images produced by the image detectors 631, 632 and/or the combined image (e.g. see FIG. 10).

As depicted, the exoscope 601 includes a housing 699 which may be configured to be held by an arm of a surgical system, for example one or more of arms 202, 410. Indeed, the video scope 402 may be adapted to include the exoscope 601. The housing 699 may include one or more apertures and/or windows and the like adjacent the objective lens 643, as well as electrical connections and the like.

Figure 9:
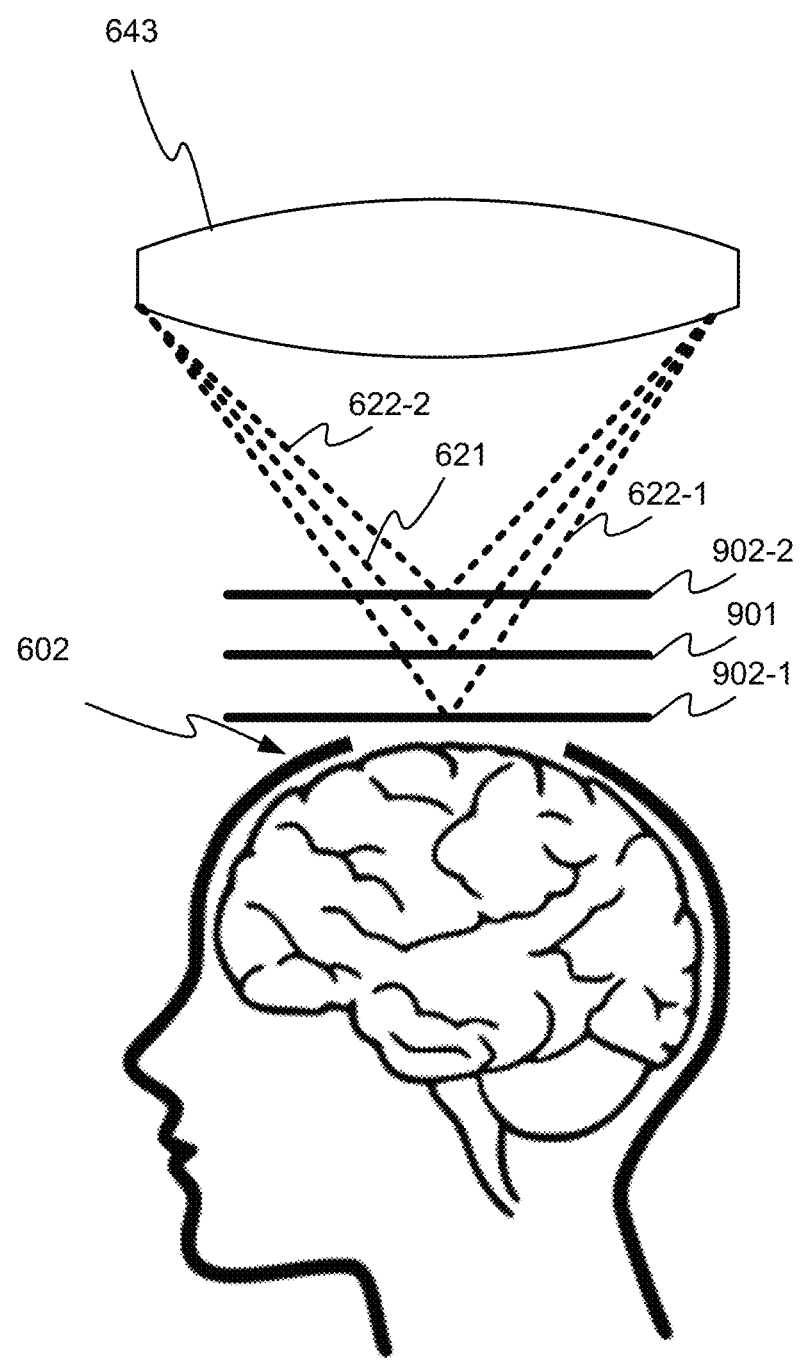
FIG. 9 depicts image planes of the exoscope of FIG. 6, according to non-limiting implementations.

Attention is next directed to FIG. 9 which schematically depicts the sample 602, the objective lens 643 and the three optical paths 621, 622-1, 622-2 as they focus at the sample 602, as well as respective image planes 901, 902-1, 902-2 located at a focal length of the three optical paths 621, 622-1, 622-2. While in FIG. 9, the image planes 901, 902-1, 902-2 are not located directly at a surface of the sample 602, it is understood that this depiction is for clarity only and the image planes 901, 902-1, 902-2 are located at the surface of the sample 602.

The image plane 901 is generally in a fixed position as the optical path 621 is fixed. Hence, the image plane 901 may interchangeably be referred to as the fixed image plane 901 of the first set of optical devices 611 and/or the first optical path 621.

However, depending on a length of the second optical path 622 (e.g. as controlled via the controller 680 controlling the variable device 655), the image plane of the second optical path 622 may change between the image plane 902-1 (e.g. when the second optical path 622 is set to the second optical path 622-1) and the image plane 902-2 (e.g. when the second optical path 622 is set to the second optical path 622-2). Hence, the image planes 902-1, 902-2 may interchangeably be referred to as the variable image plane 902 of the second set of optical devices 612 and/or the second optical path 622.

Hence a first image acquired by the first image detector 631 at the image plane 901 may be combined with a second image acquired by the second image detector 632 at one or more of the image planes 902-1, 902-2 and/or image planes therebetween. In other words, in some examples, the image plane of the second optical path 622 may be changed to any image plane between the image planes 902-1, 902-2.

Figure 10:
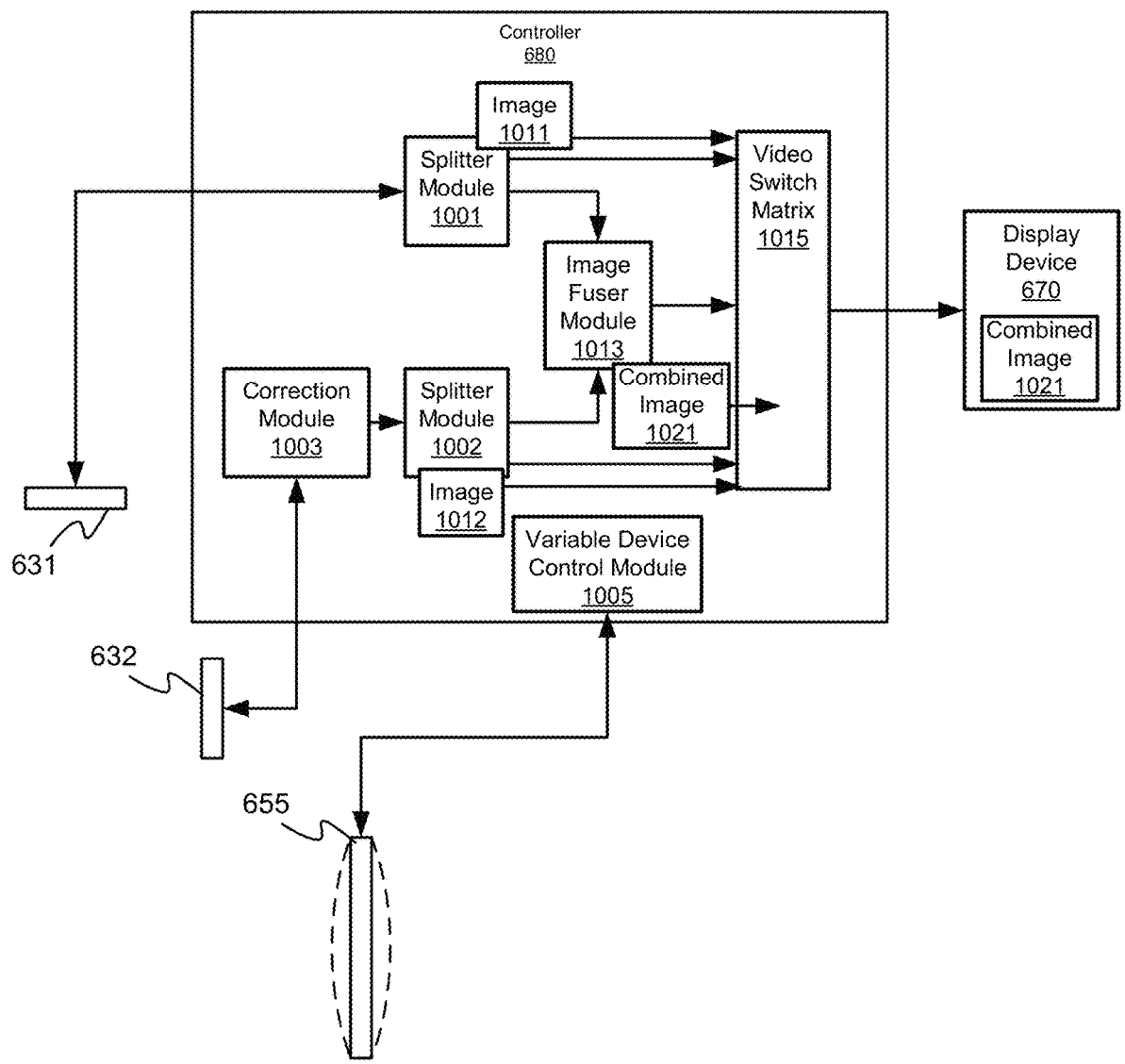
FIG. 10 depicts a schematic block diagram of a controller of the exoscope of FIG. 6, according to non-limiting implementations.

Attention is next directed to FIG. 10 which depicts a schematic block diagram of the controller 680, the image detectors 631, 632, the at least one variable device 655 and the display device 670 of the exoscope 601 (e.g. as depicted in FIGS. 6-8); while not all the components of the exoscope 601 are depicted in FIG. 10, they are nonetheless assumed to be present.

As depicted, the controller 680 comprises two splitter modules 1001, 1002, the first splitter module 1001 in communication with the first image detector 631, and the second splitter module 1002 in communication with the second image detector 632 via a correction module 1003. The correction module 1003 is configured to correct images from the second image detector 632 for magnification, distortion and spatial offsets relative to the images from the first image detectors 631. For example, the images produced by each of the image detectors 631, 632 may have differences in magnification, and relative position of features of the sample 602, and the correction module 1003 corrects for these differences based, for example, on differences in the images previously determined during a calibration step. Alternatively, and/or in addition to the correction module 1003, the first splitter module 1001 may be in communication with the first image detector 631 via a similar correction module. However, the correction module 1003, and the like, may be optional.

As depicted, the controller 680 further comprises a variable device control module 1005 configured to communicate with components of the at least one variable device 655 to change the length of the second optical path 622. The variable device control module 1005 may be controlled by an input device, as described above. For example, when the at least one variable device 655 comprises a liquid-based varifocal lens, the variable device control module 1005 may control an amount of liquid in the varifocal lens. Similar, when the at least one variable device 655 comprises apparatus moving the second image detector 632 and/or a moveable lens, the variable device control module 1005 may control the position of the second image detector 632 and/or the moveable lens.

The variable device control module 1005 may hence control at least one variable device 655 to select an image plane 902 (e.g. as depicted in FIG. 9), and each of the splitter modules 1001, 1002 may communicate with the respective image detectors 631, 632 to produce a respective image 1011, 1012 (e.g. each having a different depth of field) as described above, the image 1012 optionally corrected using the correction module 1003.

Each of the splitter modules 1001, 1002 communicate with an image fuser module 1013 and a video switch matrix 1015. The image fuser module 1013 receives both the images 1011, 1012 and produces a combined image 1021 of the images 1011, 1012 (e.g. the image fuser module 1013 combines and/or "fuses" the images 1011, 1012 to produce the combined image 1021). As described above, the controller 680 may be configured to correct at least one of the first image 1011 and the second image 1012 prior to combining the first image 1011 and the second image 1012 to correct for one or more of magnification and spatial offsets.

The combined image 1021 has an extended depth of field as compared to the images 1011, 1012. For example, the image fuser module 1013 may combine in-focus regions of the first image 1011 with in-focus regions of the second image 1012 to produce the combined image 1021, which may hence generally include more in-focus regions than either of the images 1011, 1012 alone.

The image fuser module 1013 is also in communication with a video switch matrix 1015. The video switch matrix 1015 is in communication with the display device 670. The video switch matrix 1015 receives both the images 1011, 1012 and the combined image 1021; the video switch matrix 1015 may be used to selectively switch between one of the images 1011, 1012, 1021 for rendering at the display device 670, for example under control of graphic user interface and/or an input device operated by a surgeon and the like. In yet further examples, the video switch matrix 1015 may be used to rapidly switch between the images 1011, 1012 for rendering at the display device 670, for example at frame rate where a human eye may combine the images 1011, 1012 into a pseudo-three-dimensional image, such frame rates greater than or equal to about 20 frames per second.

Hence, the controller 680 may be further configured to control the display device 670 to change between rendering the: first image 1011, the second image 1012 and the combined image 1021.

While the exoscope 601 has been described with respect to specific components, the exoscope 601 may be adapted to include other types of components.

Figure 11:
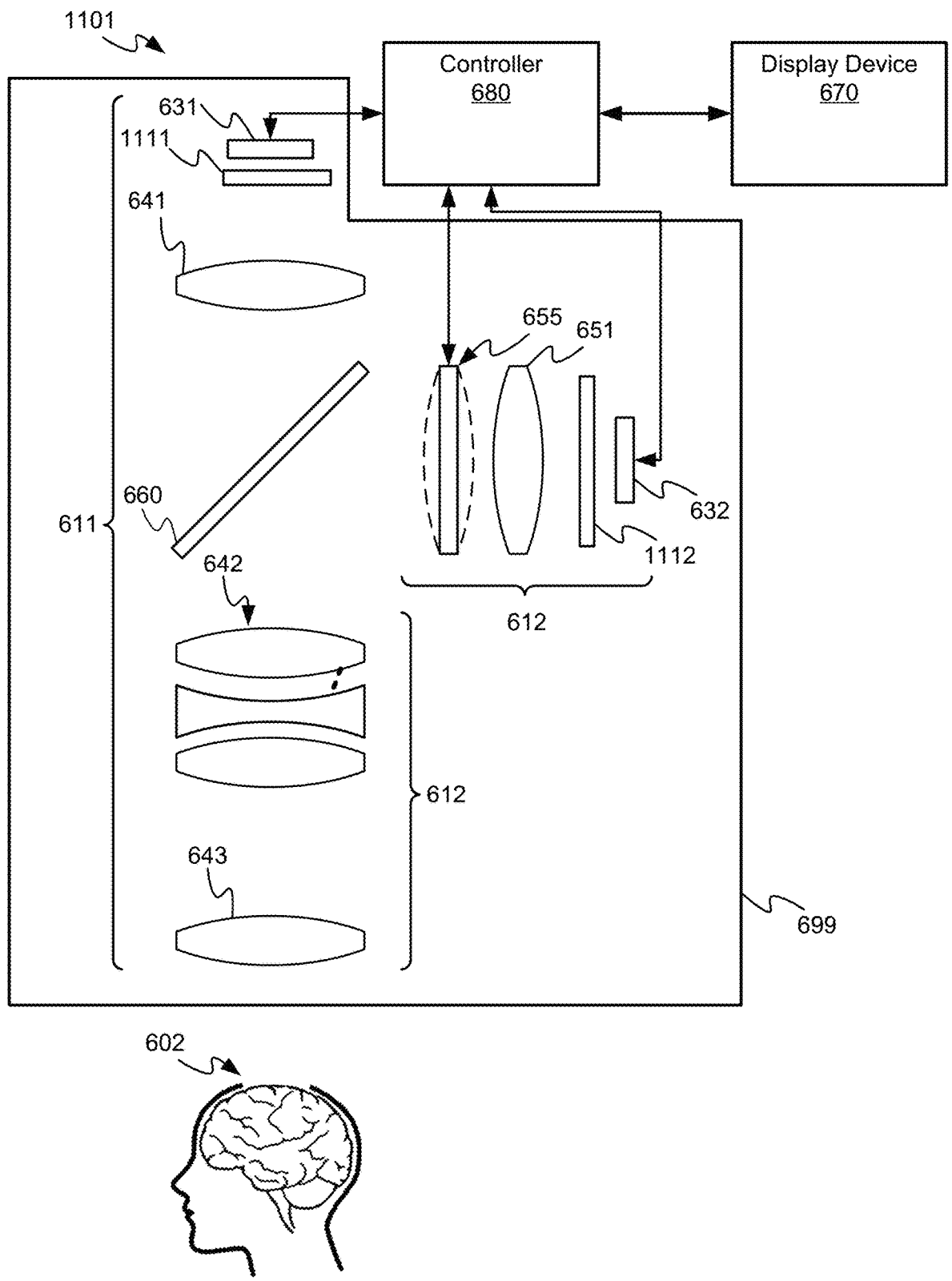
FIG. 11 depicts an exoscope similar to the exoscope of FIG. 6, adapted to include optical filters, according to non-limiting implementations.

For example, attention is next directed to FIG. 11 which depicts an exoscope 1101 that is substantially similar to the exoscope 601 with like components having like numbers. However, in contrast to the exoscope 601, at the exoscope 1101, each of first set of optical devices 611 and the second set of optical devices 612 have been adapted to include a respective optical filter 1111, 1112 for filtering respective light of one or more of the first image 1011 (e.g. as in FIG. 10) and the second image 1012 (e.g. as in FIG. 10). While each of the optical filters 1111, 1112 are located adjacent a respective image detector 631, 632, the optical filters 1111, 1112 may be located in any portion of the respective optical paths 621, 622 that do not overlap.

While FIG. 11 depicts two optical filters 1111, 1112 at the exoscope 1101, the exoscope 1101 may comprise only one of the optical filters 1111, 1112. Further, the optical filters 1111, 1112 may transmit the same wavelengths (e.g. have the same bandwidth) or different wavelengths (e.g. have different bandwidths). When the optical filters 1111, 1112 have the same bandwidth, the optical filters 1111, 1112 may be replaced with a single optical filter in a portion of the optical paths 621, 622 (see FIGS. 6-8, for example) that overlap.

Figure 12:
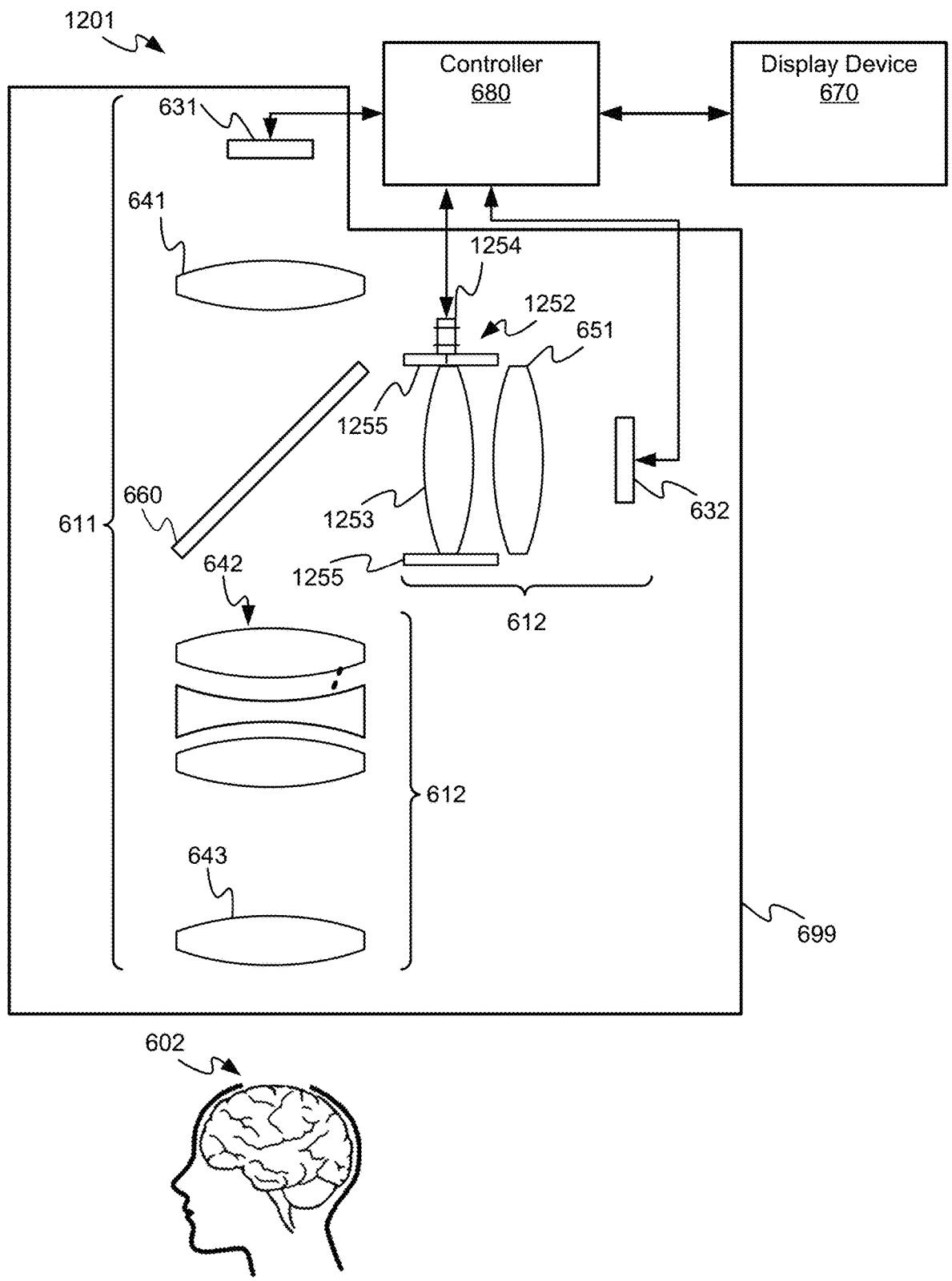
FIG. 12 depicts an exoscope similar to the exoscope of FIG. 6, adapted to include a moveable lens, according to non-limiting implementations.

Further alternatives for the at least one variable device 655 are also within the scope of the present specification. For example, attention is next directed to FIG. 12 which depicts an exoscope 1201 that is substantially similar to the exoscope 601 with like components having like numbers. However, in contrast to the exoscope 601, at the exoscope 1201, the liquid-based varifocal lens of the at least one variable device 655 has been replaced with at least one variable a variable device 1252 comprising a moveable lens 1253 and an apparatus for moving the moveable lens 1253 along the second optical path 622 (e.g. as best depicted in FIG. 7 and FIG. 8). For example, as depicted, the apparatus for moving the moveable lens 1253 along the second optical path 622 comprises a motor 1254, such as a stepper motor and the like, and a track 1255 (e.g. as depicted on two sides of the moveable lens 1253) and/or a rack-and-pinion apparatus, and the like. The motor 1254 generally moves the moveable lens 1253 along the track 1255 under control of the controller 680 (e.g. using the variable device control module 1005). Hence, with reference to FIG. 9, the image plane 902 of the second optical path 622 may be varied by moving the moveable lens 1253.

Figure 13:
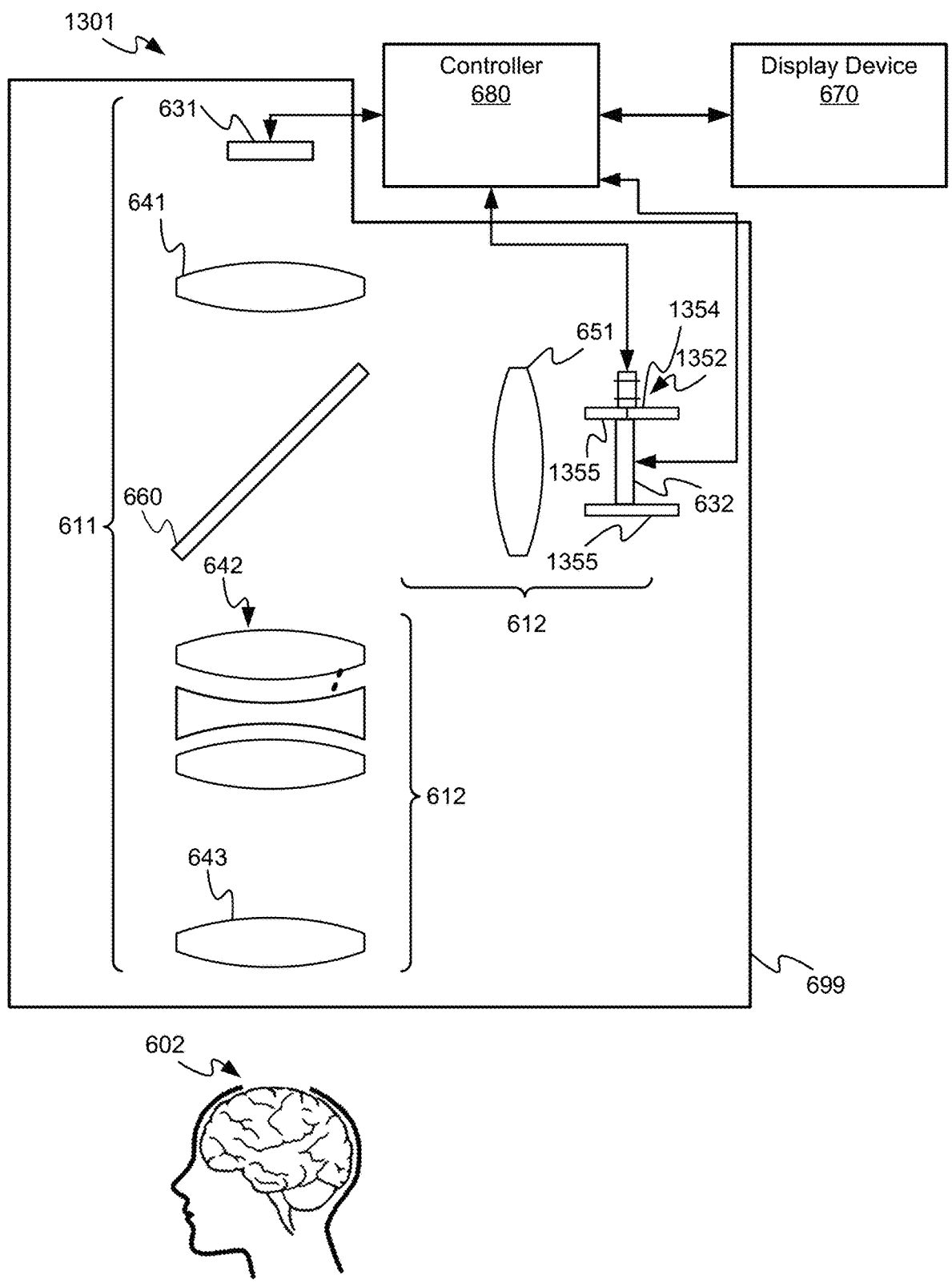
FIG. 13 depicts an exoscope similar to the exoscope of FIG. 6, adapted to include a moveable image detector, according to non-limiting implementations.

Further alternatives for the at least one variable device 655 are also within the scope of the present specification. For example, attention is next directed to FIG. 13 which depicts an exoscope 1301 that is substantially similar to the exoscope 601 with like components having like numbers. However, in contrast to the exoscope 601, at the exoscope 1301, the liquid-based varifocal lens of the at least one variable device 655 has been replaced with at least one variable a variable device 1352 comprising an apparatus for moving the second image detector 632 along the second optical path 622 (as best depicted in FIG. 7 and FIG. 8). For example, as depicted, the apparatus for moving the second image detector 632 along the second optical path 622 comprises a motor 1354, such as a stepper motor and the like, and a track 1355 (e.g. as depicted on two sides of the second image detector 632) and/or a rack-and-pinion apparatus, and the like. The motor 1354 generally moves the second image detector 632 along the track 1355 under control of the controller 680 (e.g. using the variable device control module 1005). Hence, with reference to FIG. 9, the image plane 902 of the second optical path 622 may be varied by moving the second image detector 632.

Indeed, any of the variable devices, 655, 1252, 1352 and/or any other variable devices for changing a length of the optical path 622 may be combined in an exoscope. For example, components and functionality for moving the second image detector 632 and/or moving the moveable lens 1253 and/or changing the focal length of the liquid-based varifocal lens (e.g. the variable device 655) may be combined in one exoscope. Indeed, in some examples, components and functionality for moving the second image detector 632 and one of moving the moveable lens 1253 and changing the focal length of the liquid-based varifocal lens (e.g. the variable device 655) may be combined to assist in focusing the second image 1012 on the second image detector 632. Indeed, in some examples, the focusing lens 651 may also be moveable to assist in focusing the second image 1012 on the second image detector 632.

Figure 14:
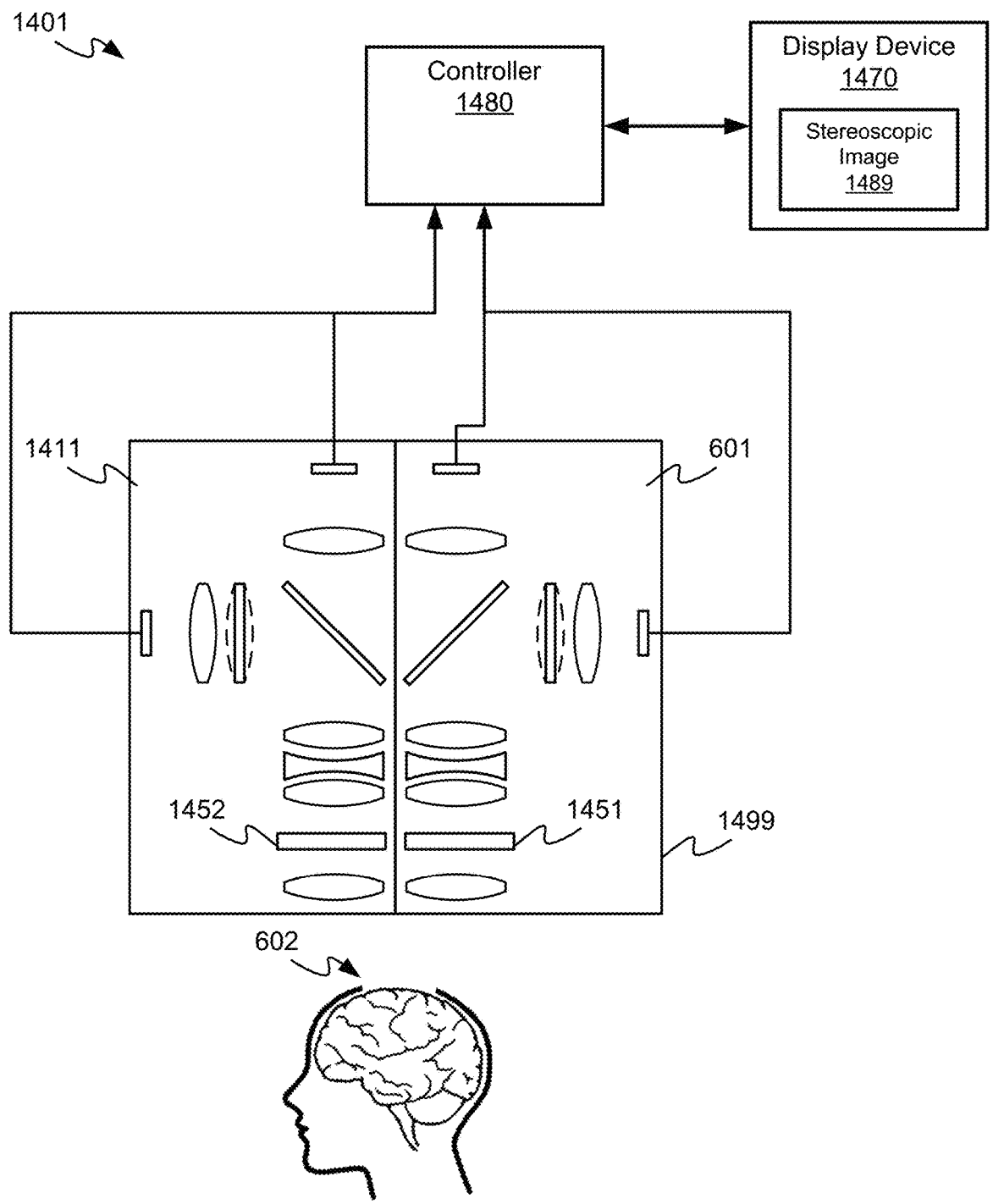
FIG. 14 depicts a three-dimensional image detector that includes two exoscopes similar to the exoscope of FIG. 6, according to non-limiting implementations.

In some examples, exoscopes described herein may be combined into three-dimensional image detectors. For example, attention is next directed to FIG. 14 which schematically depicts a three-dimensional image detector 1401, that includes the exoscope 601 (e.g. a first exoscope) and a second exoscope 1411 that is substantially similar to the exoscope 601. While the components of the exoscopes 601, 1411 are not numbered, the components of each of the exoscopes 601, 1411 are similar to as described above with respect to FIG. 6, FIG. 7 and FIG. 8. However, the exoscopes 601, 1411 are arranged relative to each other to acquire respective combined images of the sample 602, each of the respective combined images from each of the exoscopes 601, 1411 viewable together (e.g. respectively by a left eye and a right eye of a viewer) as a three-dimensional image.

Hence, the first set of optical devices 611, the second set of optical devices 612, the image detectors 631, 632, and the beamsplitter 660 (e.g. of the exoscope 601) comprise a first channel of the three-dimensional image detector 1401, the three-dimensional image detector 1401 further comprising a second channel (e.g. produced by the second exoscope 1411) similar to the first channel, each of the first channel and the second channel configured to produce respective images of a three-dimensional image.

Furthermore, the three-dimensional image detector 1401 comprises a display device 1470 and a controller 1480 each respectively similar to the display device 607 and the controller 680, however the display device 1470 is adapted to render three-dimensional images and the controller 1480 is configured to produce the three-dimensional images, for example by producing a respective combined image for each of the exoscopes 601, 1411, as described above. Hence, the controller 1480 is in communication with respective first image detectors (e.g. the first image detector 631) and respective second image detectors (e.g. the second image detector 632) at each of the exoscopes 601, 1411; while not depicted, the controller 1480 may be further configured to control respective at least one variable devices (e.g. the at least one variable device 652) at each of the exoscopes 601, 1411.

As depicted, each of the exoscopes 601, 1411 comprise respective optional optical filter 1451, 1452, for example in the portion of each exoscope 601, 1411 having a combined optical path, though the each exoscope 601, 1411 may include optical filters similar to the optical filters 1111, 1112 (e.g. as depicted in FIG. 11). The optical filters 1451, 1452 may have the same or different bandwidths, for example for filtering light from the sample 602 for three-dimensional fluorescence imaging and/or for three-dimensional fluorescence-white light combined images (for example, each optical filter 1451, 1452 could have a slightly different bandwidth).

Furthermore the controller 1480 is generally configured to control the at least one variable device of each of the first exoscope 601 and the second exoscope 1411 to change the length of the variable optical path length and the position of the variable image plane relative to the fixed image plane; control the first image detector of each of the first exoscope 601 and the second exoscope 1411 to acquire the first image at the fixed image plane; control the second image detector of each of the first exoscope 601 and the second exoscope 1411 to acquire the second image at the variable image plane; generate a combined image of the first image and the second image of each of the first exoscope 601 and the second exoscope 1411; and control the display device 1470 to render the combined image of each of the first exoscope 601 and the second exoscope 1411 as a stereoscopic image 1489.

As depicted, the three-dimensional image detector 1401 includes a housing 1499 which may be configured to be held by an arm of a surgical system, for example one or more of arms 202, 410. Indeed, the video scope 402 may be adapted to include the three-dimensional image detector 1401.

While present examples have been described with respect to varying an optical path length and/or an image plane via one or more of a varifocal lens, a liquid-based varifocal lens, a moveable sensor, and a moveable lens, other types of suitable devices for varying an optical path length and/or an image plane are within the scope of the present specification. For example, with reference to FIG. 6, the at least one variable device 655 may alternatively include a moveable plenoptic lens (e.g. an array of microlenses with different regions having different focal lengths, a position of the regions with respect to the second image sensor 632 controlled a via one or more stepper motors), and/or an optic-wheel (e.g. a plurality of lenses on wheel with different lenses having different focal lengths, a position of the plurality of lenses with respect to the second image sensor 632 controlled a via one or more stepper motors), and the like.

While present examples are described with respect to exoscopes, at least the optical components described herein may be adapted for use in an endoscope and/or a surgical microscope. For example, the sets of optical devices 611, 612 (and similarly optical devices of the exoscope 1411) may be adapted for use in an endoscope and/or a surgical microscope, and/or the housings 699, 1499 may be replaced with and/or adapted for endoscope housings and/or a surgical microscope housings.

Provided herein is an exoscope with extended depth of field with two optical paths, each of which include a respective image detector, and in which a variable device is used to change an optical path length of one of the optical paths to extend the depth of field of a combined image produced from respective images of the image detectors, the depth of field of the combined image extended with respect to the depths of field of each of the individual images of the image detectors.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A method comprising:
    at an exoscope comprising: a first image detector and a second image detector; respective optical filters to filter respective light directed to the first image detector and the second image detector; optical devices, forming: a first optical path having a fixed path length and a fixed image plane; and a second optical path having a variable optical path length and a variable image plane adjacent the fixed image plane; at least one variable device configured to change a length of the variable optical path length and a position of the variable image plane relative to the fixed image plane; a beamsplitter positioned to: combine the first optical path and the second optical path between the beamsplitter and both the fixed image plane and the variable image plane; and direct the respective light from each of the first optical path and the second optical path respectively towards the first image detector and the second image detector; and a display device,
        controlling, at the exoscope, the at least one variable device to change the length of the variable optical path length and the position of the variable image plane relative to the fixed image plane;
        controlling, at the exoscope, the first image detector to acquire the first image at the fixed image plane;
        controlling, at the exoscope, the second image detector to acquire the second image at the variable image plane;
        generating, at the exoscope, a combined image of the first image and the second image; and
        controlling, at the exoscope, the display device to render the combined image.
2. The method of claim 1, wherein the at least one variable device comprises a liquid-based varifocal lens configured to change between a parallel plane mode and a lens mode.
3. The method of claim 1, wherein the at least one variable device comprises a varifocal lens having a variable focal length.
4. The method of claim 1, wherein the at least one variable device comprises a moveable lens and an apparatus for moving the moveable lens along the second optical path.
5. The method of claim 1, wherein the at least one variable device comprises an apparatus for moving the second image detector along the second optical path.
6. The method of claim 1, wherein the first image detector and the second image detector have different respective wavelength sensitivity ranges.
7. The method of claim 1, further comprising controlling the display device to change between rendering the: first image, the second image and the combined image.
8. The method of claim 1, wherein one or more of the first optical path and the second optical path include an optical filter for filtering respective light of one or more of the first image and the second image.
9. The method of claim 1, further comprising correcting at least one of the first image and the second image prior to combining the first image and the second image to correct for one or more of magnification and spatial offsets.
10. The method of claim 1, wherein the second image detector is configured to acquire fluorescence images at the variable image plane.
11. A method comprising:
    at a three-dimensional image detector comprising: a first exoscope and a second exoscope, each of the first exoscope and the second exoscope comprising: a first image detector and a second image detector; and respective optical filters to filter respective light directed to the first image detector and the second image detector; optical devices forming: a first optical path having a fixed path length and a fixed image plane; a second optical path having a variable optical path length and a variable image plane adjacent the fixed image plane of the first optical path; at least one variable device configured to change a length of the variable optical path length and a position of the variable image plane relative to the fixed image plane; a beamsplitter positioned configured to: combine the first optical path and the second optical path between the beamsplitter and both the fixed image plane and the variable image plane; and direct respective light from each of the first optical path and the second optical path respectively towards the first image detector and the second image detector; and a display device,
        controlling, at the three-dimensional image detector, the at least one variable device of each of the first exoscope and the second exoscope to change the length of the variable optical path length and the position of the variable image plane relative to the fixed image plane;
        controlling, at the three-dimensional image detector, the first image detector of each of the first exoscope and the second exoscope to acquire the first image at the fixed image plane;
        controlling, at the three-dimensional image detector, the second image detector of each of the first exoscope and the second exoscope to acquire the second image at the variable image plane;
        generating, at the three-dimensional image detector, a combined image of the first image and the second image of each of the first exoscope and the second exoscope; and controlling, at the three-dimensional image detector, the display device to render the combined image of each of the first exoscope and the second exoscope as a stereoscopic image.

12. The method of claim 11, wherein the at least one variable device of each of the first exoscope and the second exoscope comprises a liquid-based varifocal lens configured to change between a parallel plane mode and a lens mode.

13. The method of claim 11, wherein the at least one variable device of each of the first exoscope and the second exoscope comprises a varifocal lens having a variable focal length.

14. The method of claim 11, wherein the at least one variable device of each of the first exoscope and the second exoscope comprises a moveable lens and an apparatus for moving the moveable lens along the second optical path.

15. The method of claim 11, wherein the at least one variable device of each of the first exoscope and the second exoscope comprises an apparatus for moving the second image detector along the second optical path.

16. The method of claim 11, wherein the first image detector and the second image detector of each of the first exoscope and the second exoscope have different respective wavelength sensitivity ranges.

17. The method of claim 11, wherein one or more of the first optical path and the second optical path of each of the first exoscope and the second exoscope include an optical filter for filtering respective light of one or more of the first image and the second image.

18. The method of claim 11, further comprising correcting at least one of the first image and the second image of each of the first exoscope and the second exoscope prior to combining the first image and the second image of each of the first exoscope and the second exoscope to correct for one or more of magnification and spatial offsets.

19. The method of claim 11, wherein the second image detector is configured to acquire fluorescence images at the variable image plane.

* * * * *